(12) United States Patent
Jian et al.

(10) Patent No.: US 9,492,090 B2
(45) Date of Patent: Nov. 15, 2016

(54) DETECTION OF BLOOD-VESSEL WALL ARTIFACTS

(75) Inventors: Zhongping Jian, Irvine, CA (US); Clayton M. Young, Irvine, CA (US); Feras Hatib, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 580 days.

(21) Appl. No.: 13/878,411

(22) PCT Filed: Oct. 5, 2011

(86) PCT No.: PCT/US2011/054871
§ 371 (c)(1),
(2), (4) Date: Jul. 16, 2013

(87) PCT Pub. No.: WO2012/047965
PCT Pub. Date: Apr. 12, 2012

(65) Prior Publication Data
US 2013/0324840 A1  Dec. 5, 2013

Related U.S. Application Data

(60) Provisional application No. 61/391,430, filed on Oct. 8, 2010.

(51) Int. Cl.
*A61B 6/00* (2006.01)
*A61B 5/00* (2006.01)
(Continued)

(52) U.S. Cl.
CPC ........... *A61B 5/0084* (2013.01); *A61B 5/6852* (2013.01); *A61B 5/6886* (2013.01); *A61B 5/7203* (2013.01); *A61B 5/742* (2013.01);
(Continued)

(58) Field of Classification Search
CPC .... A61B 5/0084; A61B 5/027; A61B 5/065; A61B 5/1459; A61B 5/6852; A61B 5/7405; A61B 5/742; A61B 5/7203; A61B 5/6886; A61B 5/7221; A61M 25/01
USPC .................................................. 600/473–480
See application file for complete search history.

(56) References Cited

U.S. PATENT DOCUMENTS 4,523,279 A    6/1985 Sperinde et al.
5,647,359 A    7/1997 Kohno et al.
(Continued)

FOREIGN PATENT DOCUMENTS

WO    2009079626 A1    6/2009

OTHER PUBLICATIONS

European Office Action, May 8, 2014.
(Continued)

*Primary Examiner* — Sanjay Cattungal
(74) *Attorney, Agent, or Firm* — Michael Crapenhoft

(57) ABSTRACT

The present application concerns detecting catheter proximity to a blood-vessel wall and blood-vessel wall artifacts associated therewith. In one embodiment, a light source, in a catheter, can be used to project light into the blood vessel. An intensity associated with at least one light wavelength that interacted with blood can be measured. Based on the measured intensity, a determination can be made regarding blood-vessel wall artifacts due to the catheter tip proximity to a blood-vessel wall. Feedback can be provided to the clinician in order to assist the clinician in adjusting the catheter to optimize signal quality and minimize artifacts due to the blood-vessel wall.

17 Claims, 10 Drawing Sheets

(51) Int. Cl.
*A61M 25/01* (2006.01)
*A61B 5/027* (2006.01)
*A61B 5/06* (2006.01)
*A61B 5/1459* (2006.01)

(52) U.S. Cl.
CPC ............ *A61B5/7405* (2013.01); *A61M 25/01* (2013.01); *A61B 5/027* (2013.01); *A61B 5/065* (2013.01); *A61B 5/1459* (2013.01); *A61B 5/7221* (2013.01)

(56) References Cited

U.S. PATENT DOCUMENTS

| | | | | |
|---|---|---|---|---|
| 5,678,550 A * | 10/1997 | Bassen | ................ | A61B 5/0084 600/342 |
| 5,758,644 A * | 6/1998 | Diab | ................. | A61B 5/14552 356/41 |
| 5,995,208 A | 11/1999 | Sarge et al. | | |
| 6,096,065 A * | 8/2000 | Crowley | ............ | A61B 1/00142 600/121 |
| 7,233,817 B2 | 6/2007 | Yen | | |
| 7,580,185 B2 * | 8/2009 | Haisch | ................ | A61B 5/0066 250/461.2 |
| 8,167,794 B2 * | 5/2012 | Matsumoto | ............ | A61B 1/041 600/160 |
| 8,401,619 B2 * | 3/2013 | Lorenzo | ............... | A61B 5/0073 600/425 |
| 8,406,840 B2 | 3/2013 | Nielsen et al. | | |
| 8,870,740 B2 * | 10/2014 | Clegg | ................... | A61M 21/00 600/27 |
| 2004/0077950 A1 * | 4/2004 | Marshik-Geurts | ... | A61B 5/0086 600/475 |
| 2006/0041199 A1 * | 2/2006 | Elmaleh | ................ | A61B 5/0071 600/478 |
| 2009/0253989 A1 * | 10/2009 | Caplan | ................. | A61B 5/0062 600/467 |
| 2010/0069760 A1 * | 3/2010 | Tang | ................... | A61B 5/02007 600/478 |
| 2014/0005553 A1 * | 1/2014 | Ryan | ................... | A61B 5/0062 600/473 |

OTHER PUBLICATIONS

International Search Report, PCT/US2011/054871, Jan. 13, 2012.
Chinese Office Action, Jul. 2, 2013.
European Office Action, Nov. 7, 2014.
Office Action issued in JP Application No. 2013-532903, Sep. 18, 2015.

* cited by examiner

Software 280 implementing described techniques and tools

DETECTION OF BLOOD-VESSEL WALL ARTIFACTS

This is a U.S. national phase application, which is based on and claims priority from PCT Application Serial No. PCT/US2011/054871, filed Oct. 5, 2011, which claims priority from U.S. Provisional Patent Application Serial No. 61/391,430, filed Oct. 8, 2010.

FIELD

The present application relates to detecting catheter proximity to a blood-vessel wall and/or associated blood-vessel wall artifacts.

BACKGROUND

During the last 25 years, the art of critical care medicine has greatly changed. Specialized units for patient care, advances in technology, and a better understanding of physiology by health care practitioners have reduced morbidity and mortality. One of the earliest advances in technology that helped to drive this progress was the development of the catheter. In the early 1970's, the addition of a thermistor to the catheter allowed for rapid assessment of cardiac output. At the same time, more sophisticated monitoring systems were also being developed. As a result, more complete hemodynamic assessment could be carried out with relative ease at a patient's bedside.

With advanced technology came the requirement of advanced clinicians. For hemodynamic monitoring, catheter placement by the clinician is important for accurate measurement of total hemoglobin (tHB) and oxygen saturation and other physiological parameters. If the catheter is placed incorrectly, strong artifacts can interfere with the measurements. In particular, blood-vessel walls have optical properties that include a strong scattering profile that can create unwanted artifacts significantly interfering with hemodynamic measurements.

Currently, there are no known devices to assist clinicians with proper catheter placement within a blood vessel for the clearest and highest quality signals.

SUMMARY

The present application concerns detecting catheter proximity to a blood-vessel wall and/or blood-vessel wall artifacts. Through such detection, a clinician can be provided with audio or visual feedback in order to assist the clinician in adjusting the catheter position to optimize signal quality and minimize artifacts due to the blood-vessel wall.

In one embodiment, a light source coupled to a catheter, can be used to project and receive light into the blood vessel. An intensity associated with at least one light wavelength can be measured. Based on the measured intensity, a determination can be made whether the blood-vessel wall artifacts exceed a threshold due to catheter proximity to a blood-vessel wall.

In another embodiment, intensities of multiple wavelengths can be measured and a ratio of the intensities can be used to determine a level of blood-vessel wall artifacts. Use of multiple wavelengths can negate differences between light sources (e.g., light source strength).

In another embodiment, one or more intensities associated with the light wavelengths can be measured and compared against predetermined benchmarks to determine a level of blood-vessel wall artifacts associated with catheter location in a blood vessel.

The foregoing and other objects, features, and advantages of the invention will become more apparent from the following detailed description, which proceeds with reference to the accompanying figures.

DETAILED DESCRIPTION

Figure 1:
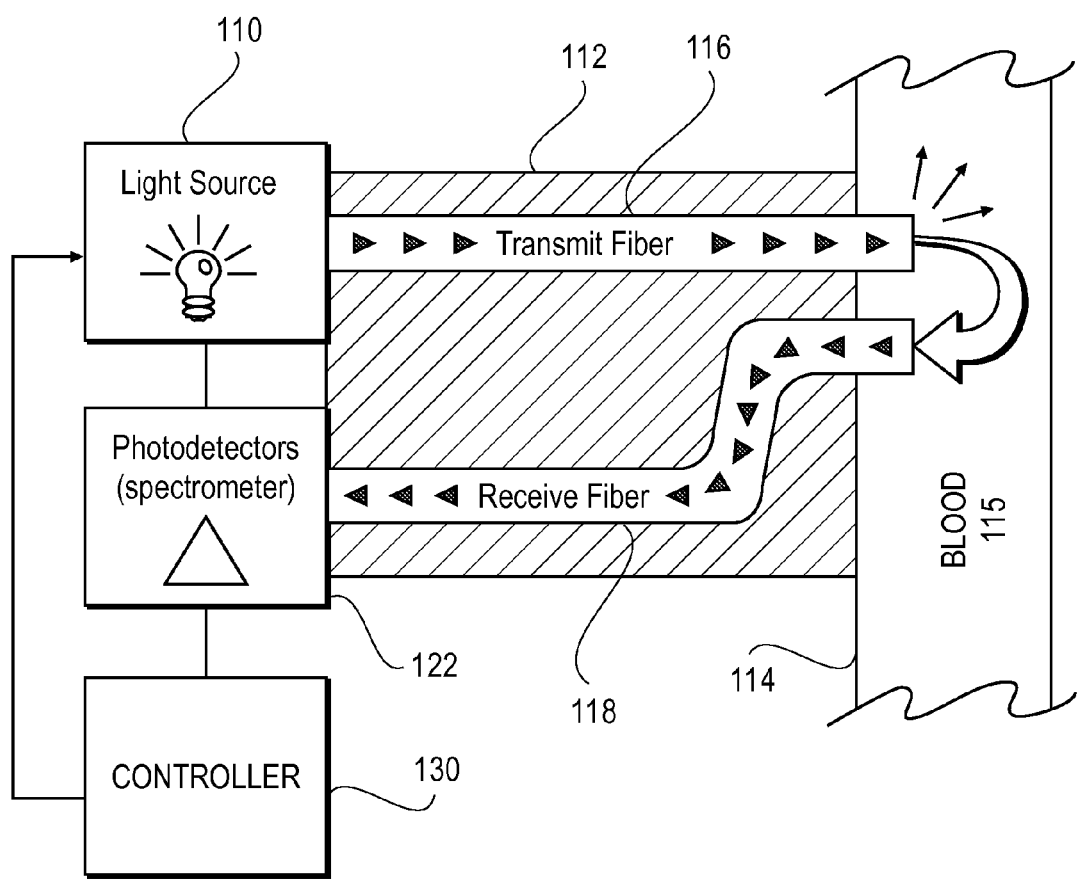
FIG. 1 is a block diagram according to one embodiment wherein a catheter is inserted into a blood vessel.

FIG. 1 shows an apparatus used to detect blood-vessel wall artifacts due to catheter proximity to a blood-vessel wall. A light source 110 is coupled to a catheter 112 inserted into a blood vessel 114. The light source 110 can be any of a variety of types, such as an LED, and typically produces light in a wavelength range between about 400 nm to about 800 nm. Other light sources can be used. Generally, the light source is turned on continuously over a discrete period of time and generates a plurality of wavelengths that are transmitted into blood 115. The catheter 112 can also be any of a variety of types, such as a central venous catheter or a pulmonary artery catheter, and can include two parallel optical fibers 116, 118. The first optical fiber 116 is a transmit fiber designed to receive light from the light source and project the light into the blood stream illuminating the blood. The second optical fiber 118 is a receive fiber capable of receiving light from the blood and delivering the light to photodetectors 122, which can be included in a spectrometer or other instrument for measuring the properties of light. Although any photodetectors can be used, the photodetectors 122 should preferably be capable of measuring intensities within the range of between about 400 nm and 1000 nm or higher. The received light is generally a combination of reflected light, scattered light and/or light transmitted through the blood. In any event, the received light carries information used to obtain parameters needed for hemodynamic monitoring, such as total hemoglobin and oxygen saturation. Ideally, the light interacts only with the blood. But, in practice, the light interacts not only with the blood, but with other objects located in the environment in which the catheter is positioned. In particular, blood-vessel wall artifacts can dominate the received light and significantly affect the calculated parameters. Incorrectly calculated blood parameters can have serious implications on patient safety, if used without caution.

A controller 130 can be coupled to the photodetectors 122 and associated instrumentation for measuring light intensity. The controller can also be coupled to the light source 110 in order to control the light source during measurements. As further described below, the controller can use the measured light intensity of at least one wavelength captured in the photodetectors 122 to determine a level of blood-vessel wall artifacts due to the proximity of the catheter tip to the blood-vessel wall. Various techniques for using light intensity to determine blood-vessel wall artifacts and catheter position are described further below.

Figure 2:
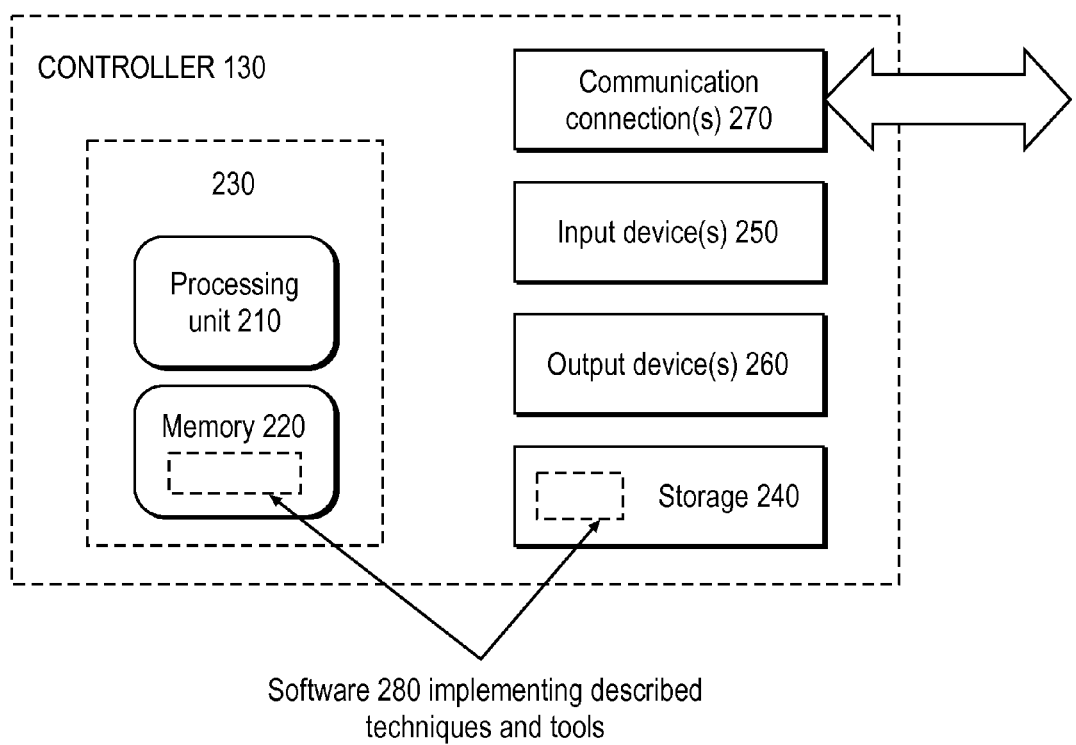
FIG. 2 is a block diagram of an example controller that can be used in FIG. 1.

FIG. 2 illustrates a generalized example of a suitable controller 130 in which the described technologies can be implemented. The controller is not intended to suggest any limitation as to scope of use or functionality, as the technologies may be implemented in diverse general-purpose or special-purpose computing environments.

With reference to FIG. 2, the controller 130 can include at least one processing unit 210 (e.g., signal processor, microprocessor, ASIC, or other control and processing logic circuitry) coupled to memory 220. The processing unit 210 executes computer-executable instructions and may be a real or a virtual processor. The memory 220 may be volatile memory (e.g., registers, cache, RAM), non-volatile memory (e.g., ROM, EEPROM, flash memory, etc.), or some combination of the two. The memory 220 can store software 280 implementing any of the technologies described herein.

The controller may have additional features. For example, the controller can include storage 240, one or more input devices 250, one or more output devices 260, and one or more communication connections 270. An interconnection mechanism (not shown), such as a bus or network interconnects the components. Typically, operating system software (not shown) provides an operating environment for other software executing in the controller and coordinates activities of the components of the controller.

The storage 240 may be removable or non-removable, and can include magnetic disks, magnetic tapes or cassettes, CD-ROMs, CD-RWs, DVDs, or any other computer-readable media that can be used to store information and which can be accessed within the controller. The storage 240 can store software 280 containing instructions for detecting blood-vessel wall artifacts associated with a catheter position in a blood-vessel wall.

The input device(s) 250 can be a touch input device such as a keyboard, mouse, pen, or trackball, a voice input device, a scanning device, or another device. The output device(s) 260 may be a display, printer, speaker, CD- or DVD-writer, or another device that provides output from the controller. Some input/output devices, such as a touchscreen, may include both input and output functionality.

The communication connection(s) 270 enables communication over a communication mechanism to another computing entity. The communication mechanism conveys information such as computer-executable instructions, audio/video or other information, or other data. By way of example, and not limitation, communication mechanisms include wired or wireless techniques implemented with an electrical, optical, RF, microwaves, infrared, acoustic, or other carrier.

Figure 3:
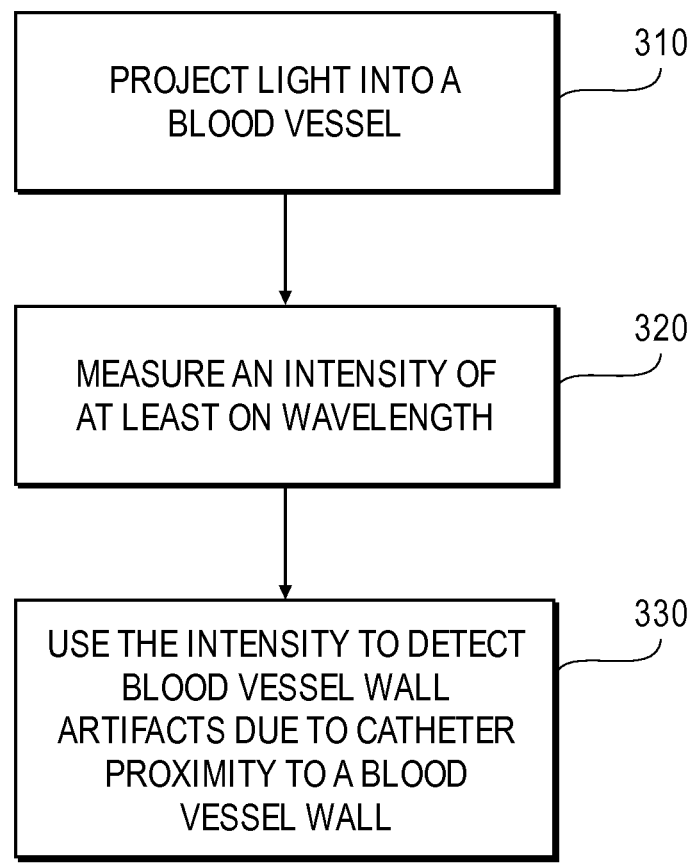
FIG. 3 is a flowchart of an embodiment for detecting blood-vessel wall artifacts.

FIG. 3 is a flowchart of an embodiment for detecting blood-vessel wall artifacts and/or catheter proximity to a blood-vessel wall. In process block 310, light is projected into the blood vessel using a catheter as already described. The light is transmitted through the transmit fiber 116 in the catheter 112 and may include one or more wavelengths, typically in the 400 nm to 850 nm range. In process block 320, an intensity is measured for at least one wavelength using photodetectors 122. The "intensity" measured is meant to be a general term associated with the emitted power per unit area or power per solid angle, depending on the particular application. In process block 330, the intensity is used to detect blood-vessel wall artifacts. Additionally, catheter position relative to the blood-vessel wall can also be estimated based on the intensity. There are a variety of techniques that can be used to detect blood-vessel wall artifacts and the present disclosure should not be considered limited to the techniques described herein.

Figure 4:
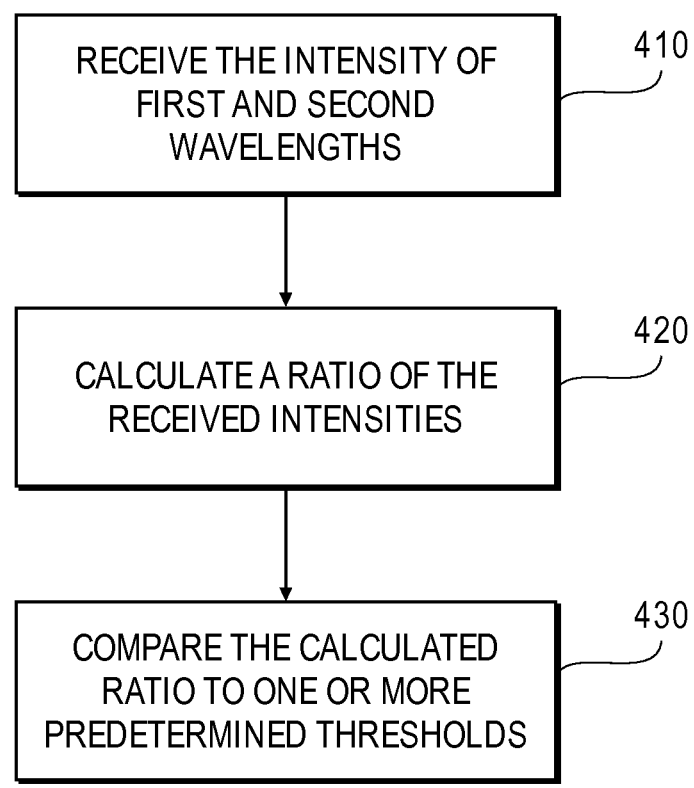
FIG. 4 is a flowchart of a method for using an intensity ratio of multiple wavelengths.

FIG. 4 shows one such technique that can be used to implement process block 330 in FIG. 3. In process block 410, intensities are received by the controller 130 from the photodetectors 122 for at least two wavelengths. In process block 420, a ratio is calculated by dividing the first intensity measurement by the second intensity measurement. Example measurements include having a first wavelength below 580 nm and the second wavelength above 720 nm. To prevent a single frequency's intensity weighting too much on the ratio, a median or mean intensity of a narrow-band region around the first and second wavelengths can be used instead. In process block 430, the calculated ratio can be compared to one or more predetermined thresholds. For example, if the ratio exceeds a threshold, it indicates that signal quality is poor as a result of the catheter tip being within an undesirable distance from the blood-vessel wall. A multistate indicator can also be used to show different levels of signal quality. For example, different thresholds can indicate different levels of signal quality. The thresholds can be determined using bench studies and/or animal studies.

Figure 5:
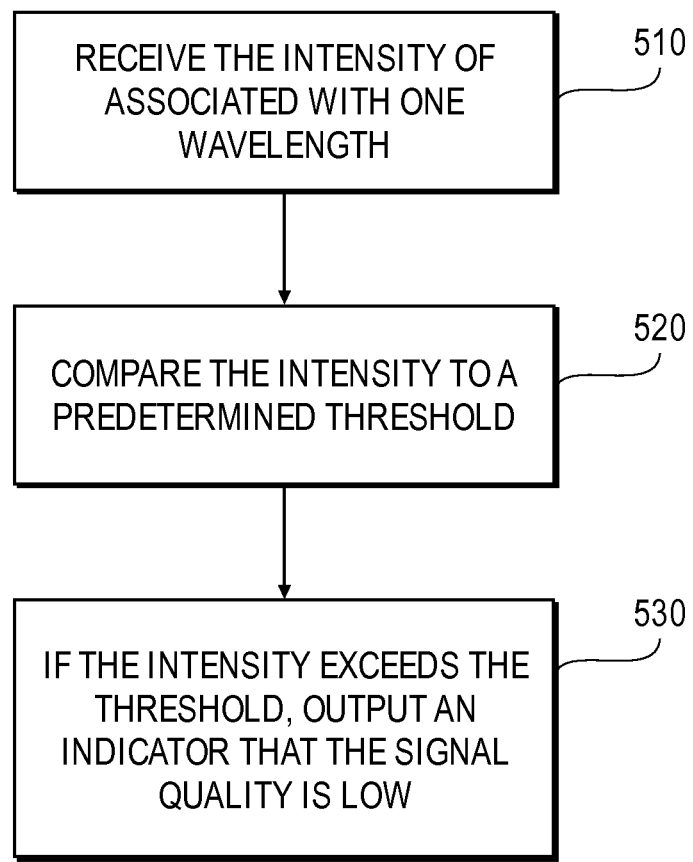
FIG. 5 is a flowchart of a method for comparing an intensity measurement to a predetermined threshold.

FIG. 5 shows another technique that can be used to implement process block 330 in FIG. 3. In process block 510, an intensity is received associated with one wavelength (or a mean or median of a range around a single wavelength). In process block 520, the intensity is compared to one or more predetermined thresholds. If the intensity exceeds the threshold, in process block 530, an indicator is output to signal that quality is low. As with FIG. 4, the thresholds can be determined using bench studies and/or animal studies. The technique of FIG. 5 allows a calculation using only a single wavelength, as opposed to FIG. 4, which requires at least two wavelengths.

Whatever technique is used, a clinician can be alerted through output device 260 using either a visual or audio indication that the catheter tip placement is not ideal. This immediate feedback can allow the clinician to dynamically adjust the catheter in order to maximize signal quality. Alternatively, any stored data can have a field indicating signal quality as a result of distance of the catheter tip to the blood-vessel wall. For example, a multi-state indicator can show various levels of signal quality (e.g., a level from 1 to 3.)

Figure 6:
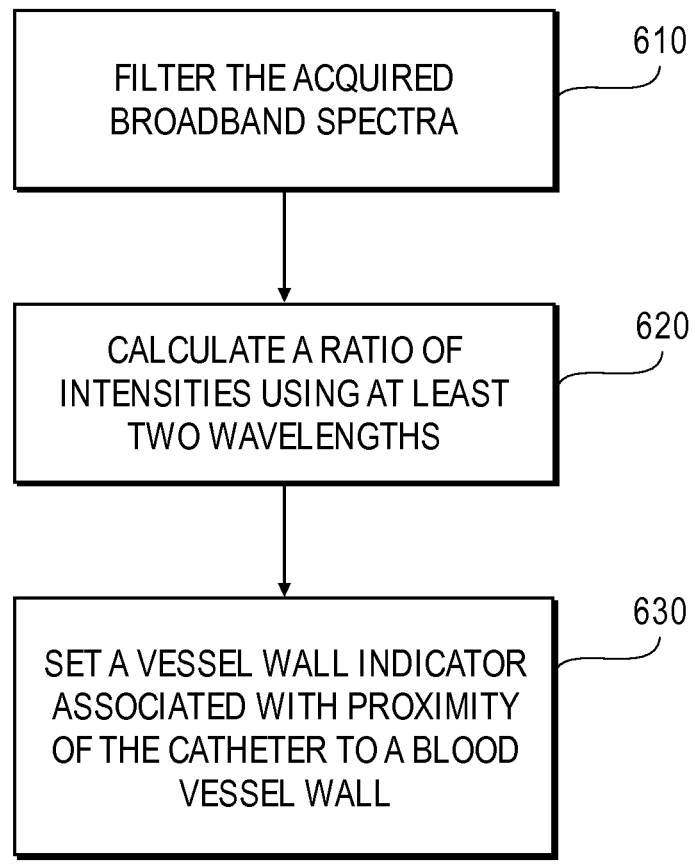
FIG. 6 is a flowchart of an embodiment for setting a vessel-wall indicator when the catheter is too close to the blood-vessel wall.
Figure 7:
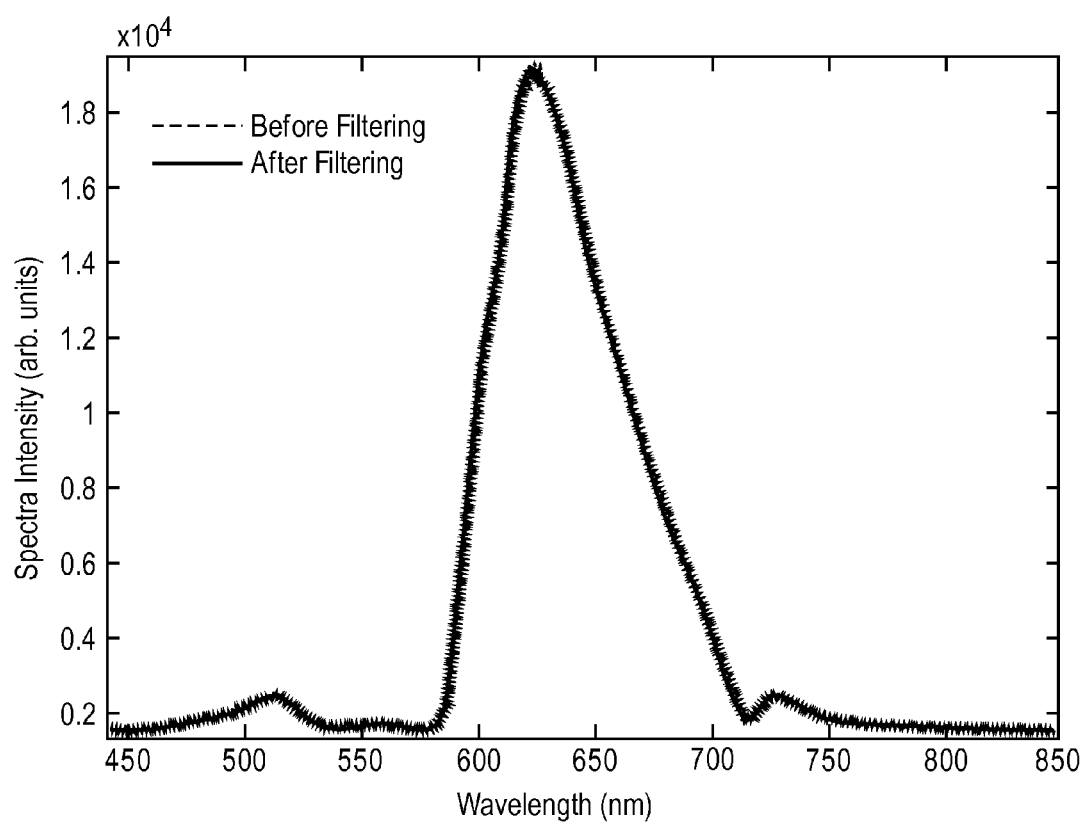
FIG. 7 is a graph illustrating filtering used in the FIG. 6.

FIG. 6 shows another embodiment of a method for detecting blood-vessel wall artifacts due to catheter proximity to a vessel wall. In process block 610, broadband spectra are acquired and filtered to attenuate background and random noise. A variety of noise reduction filters can be used depending on the particular application, including linear or non-linear filters. FIG. 7 provides an example graph showing data before and after using a filter. In process block 620, a ratio is calculated using at least two wavelength intensities. As previously described, a narrow range can also be used around two wavelength intensities. In process block 630, a vessel wall indicator is set based on the proximity of the catheter to the blood-vessel wall. Using predetermined intensity thresholds, various levels of signal quality can be output to a clinician or data file, as previously described. Additionally, catheter position can be estimated based on the intensities.

Figure 8:
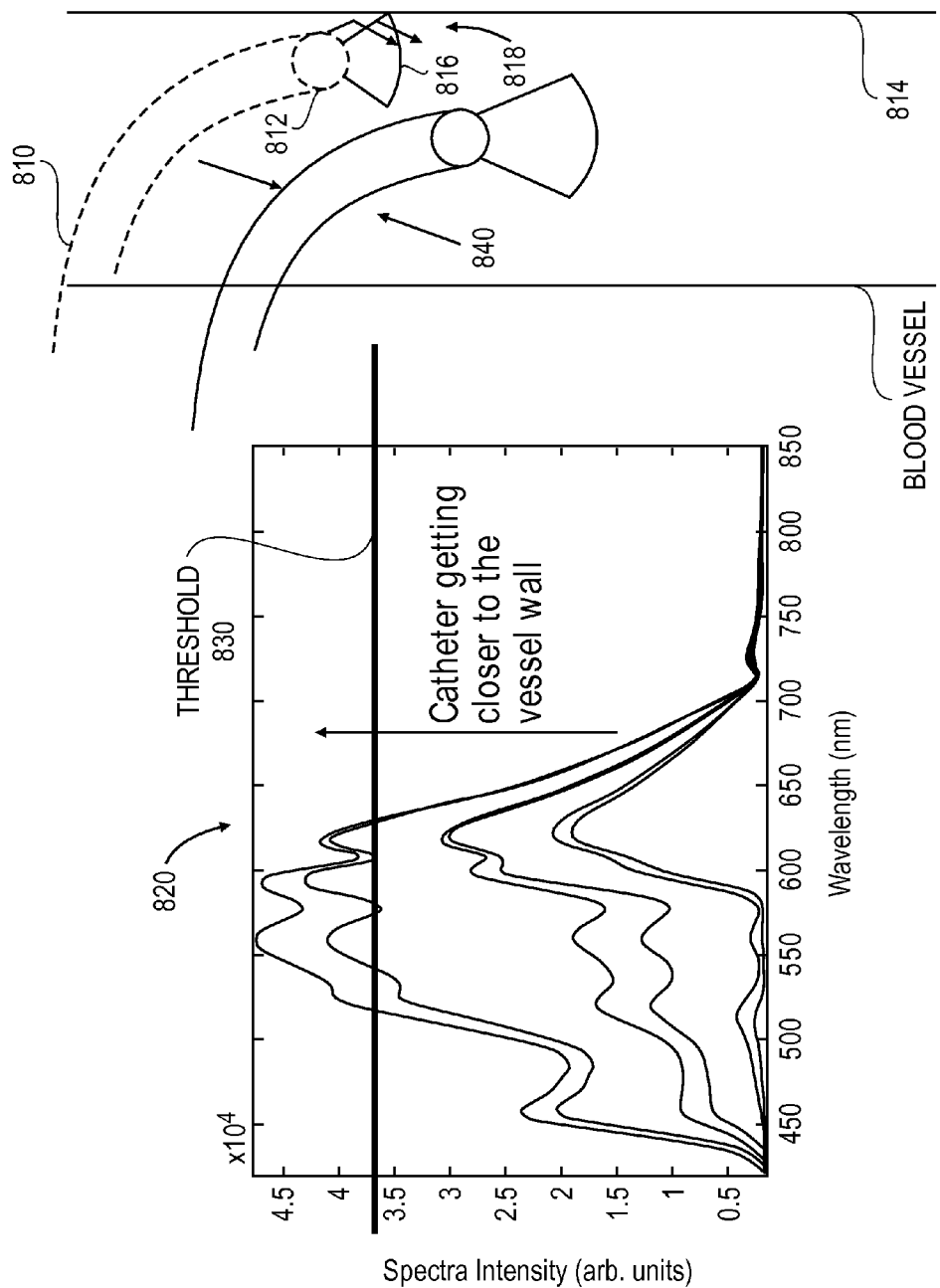
FIG. 8 shows catheter placement in a blood vessel and an associated graph with intensities changing based on catheter placement within a blood vessel.

FIG. 8 shows a catheter 810 in dashed lines that has a tip 812 adjacent a blood-vessel wall 814. Light 816 illuminated from a tip 812 of the catheter is reflected from the blood-vessel wall (as shown by arrows 818) creating unwanted artifacts that can significantly interfere with hemodynamic measurements. As shown in the graph 820, the spectral intensity of the light received through the catheter increases across a variety of wavelengths, particularly in the range of 400 nm to 1000 nm or higher with the catheter placed adjacent the wall 814. In an example embodiment, a threshold 830 can be set such that if the spectral intensity exceeds the threshold, an indicator can be provided to a clinician so that the clinician has immediate feedback on catheter tip location and placement. As a result, the clinician can move the catheter to the position shown at 840 in solid lines where the light transmitted into the blood is less affected by artifacts due to the blood-vessel walls. Such immediate feedback to the clinician ensures a high-signal quality for accurate hemodynamic measurements.

Figure 9:
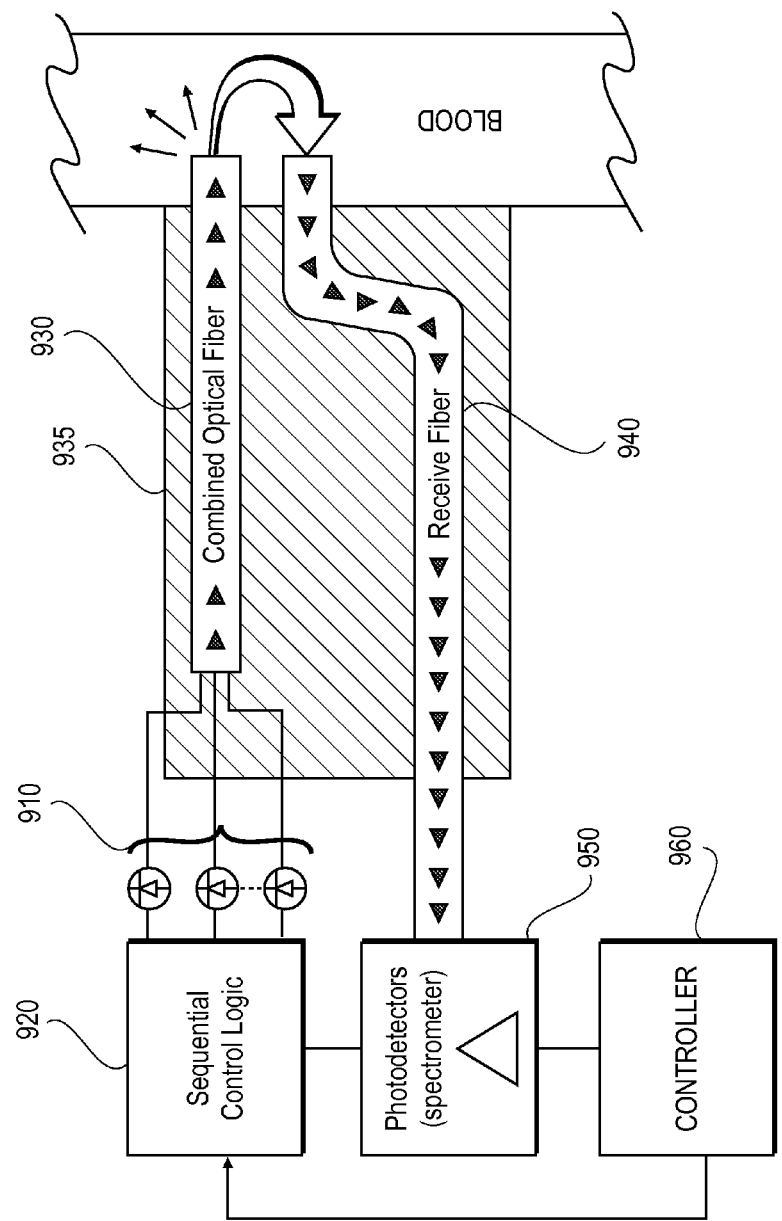
FIGS. 9 and 10 show alternative embodiments used for a light source.
Figure 10:
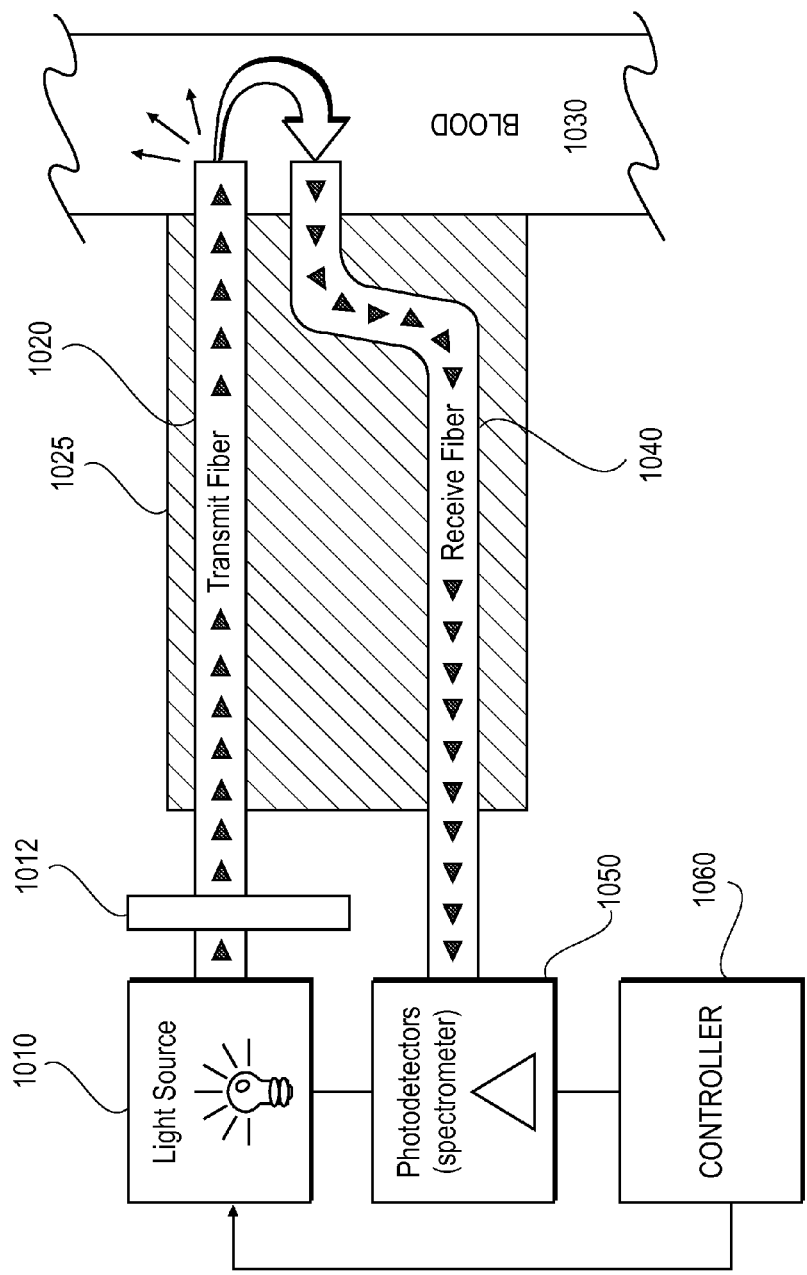

FIGS. 9 and 10 show other structures that can be used to implement the methods described herein. In FIG. 9, multiple light sources 910, such as multiple colored LEDs can be used to provide discrete wavelengths that can be time multiplexed by sequencer control logic 920 to individually turn on at different times. The discrete signals are transmitted through an optical transmit fiber 930 located in a catheter 935 into the blood and reflected into a receive fiber 940. The receive fiber 940 transmits the discrete reflected signals to a single photodetector of a spectrometer 950. Multiple photodetectors may be employed to measure the special effects of the signals. A controller 960 is coupled to the photodetectors and is used to determine blood-vessel wall artifacts and/or catheter tip location, as previously described.

In FIG. 10, single or multiple light sources 1010 may be transmitted through a wavelength filter 1012, such as a filter wheel, to provide an alternate or additional embodiment of discrete wavelengths that may be time multiplexed. The light signals are passed through the filter 1012 and transmitted through an optical fiber 1020 located in a catheter 1025 into blood 1030 and then reflected back through a receive fiber 1040 to at least one photodetector 1050. A controller 1060 is coupled to the photodetectors and is used to determine blood-vessel wall artifacts and/or catheter tip location, as previously described.

The techniques herein can be described in the general context of computer-executable instructions, such as those included in program modules, being executed in a computing environment on a target real or virtual processor. Generally, program modules include routines, programs, libraries, objects, classes, components, data structures, etc., that perform particular tasks or implement particular abstract data types. The functionality of the program modules may be combined or split between program modules as desired in various embodiments. Computer-executable instructions for program modules may be executed within a local or distributed computing environment.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable storage media (e.g., non-transitory computer-readable media, such as one or more optical media discs, volatile memory components (such as DRAM or SRAM), or nonvolatile memory components (such as hard drives)) and executed on a computer (e.g., any commercially available computer, including smart phones or other mobile devices that include computing hardware). Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. A method comprising:
projecting a light from a catheter into a blood vessel having a blood-vessel wall;
measuring a first intensity of a first wavelength associated with the light;
measuring a second intensity of a second wavelength associated with the light;
calculating a ratio of the first intensity and the second intensity;

comparing the ratio with a threshold; and
based on the comparing, determining a proximity of the catheter to the blood-vessel wall;
wherein the first wavelength is below approximately 580 nm and the second wavelength is above approximately 720 nm.

2. The method of claim 1, wherein if the ratio exceeds the threshold, outputting an indicator to indicate that the catheter is too close to the blood-vessel wall.

3. The method of claim 1, further including filtering the first wavelength to attenuate background and random noise prior to measuring the first intensity.

4. The method of claim 1, wherein the catheter includes a transmit optical fiber and a receive optical fiber.

5. The method of claim 1, wherein measuring the first intensity includes receiving the first wavelength from a receive optical fiber and using a photodetector to capture electromagnetic energy associated therewith.

6. A non-transitory computer storage medium having a computer program product stored thereon, the computer program product comprising instuctions which, when executed on at least one processor, cause the at least one processor to implement the method of claim 1.

7. The method of claim 2, wherein the indicator includes outputting a visual or audio signal to a clinician.

8. The method of claim 1, wherein projecting the light is through a transmit optical fiber in the catheter during catherization, and wherein the method further includes receiving the light after the light interacts with a blood in the blood vessel through a receive optical fiber.

9. The method of claim 8, wherein interaction of the light with the blood includes transmission, reflection and scattering of light waves.

10. The method of claim 1, wherein measuring the first intensity is performed using photodetectors.

11. The method of claim 7 further comprising:
dynamically and interactively modifying the visual or audio output signal to the clinician, as the clinician moves the catheter.

12. The method of claim 1, wherein the first wavelength is above approximately 400 nm and the second wavelength is below approximately 850 nm.

13. An apparatus comprising:
a catheter including a transmit optical fiber and a receive optical fiber;
a light source coupled to the transmit optical fiber for transmitting a light into a blood vessel having a blood and a blood-vessel wall;
one or more photodetectors coupled to the receive optical fiber for receiving the light after the light interacts with the blood; and
a controller coupled to the one or more photodetectors and configured to:
measure a first intensity of a first wavelength associated with the light;
measure a second intensity of a second wavelength associated with the light;
calculate a ratio of the first intensity and the second intensity;
compare the ratio with a threshold; and
based on comparing, determine a proximity of the catheter to the blood-vessel wall;
wherein the first wavelength is below approximately 580 nm and the second wavelength is above approximately 720 nm.

14. The apparatus of claim 13, wherein the light source includes one or more LEDs.

15. The apparatus of claim 13, further including an output device coupled to the controller for providing a visual or audio signal to a clinician based on the proximity.

16. The apparatus of claim 13, wherein the controller dynamically and interactively modifies a visual or audio output signal indicative of the proximity of the catheter to the blood-vessel wall, as a clinician moves the catheter.

17. The apparatus of claim 13, wherein the first wavelength is above approximately 400 nm and the second wavelength is below approximately 850 nm.

* * * * *